United States Patent
Liu

(10) Patent No.: US 11,273,135 B2
(45) Date of Patent: *Mar. 15, 2022

(54) METHODS FOR USING STABILIZED SULFORAPHENE

(71) Applicant: Shaoyun Liu, Stony Brook, NY (US)

(72) Inventor: Shaoyun Liu, Stony Brook, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/521,111

(22) Filed: Jul. 24, 2019

(65) Prior Publication Data

US 2019/0343784 A1   Nov. 14, 2019

Related U.S. Application Data

(63) Continuation-in-part of application No. 16/479,288, filed as application No. PCT/US2019/017150 on Feb. 8, 2019.

(60) Provisional application No. 62/628,353, filed on Feb. 9, 2018.

(51) Int. Cl.
| | |
|---|---|
| *A61K 31/185* | (2006.01) |
| *A61P 21/00* | (2006.01) |
| *A61K 47/40* | (2006.01) |
| *A61K 47/69* | (2017.01) |
| *A61P 25/14* | (2006.01) |
| *A61P 17/06* | (2006.01) |
| *A61P 21/06* | (2006.01) |
| *A61K 31/26* | (2006.01) |

(52) U.S. Cl.
CPC ............ *A61K 31/185* (2013.01); *A61K 31/26* (2013.01); *A61K 47/40* (2013.01); *A61K 47/6951* (2017.08); *A61P 17/06* (2018.01); *A61P 21/00* (2018.01); *A61P 21/06* (2018.01); *A61P 25/14* (2018.01)

(58) Field of Classification Search
CPC ............................. A61K 31/185; A61P 21/00
See application file for complete search history.

(56) References Cited

U.S. PATENT DOCUMENTS

| 9,610,258 B2 | 4/2017 | McWherter et al. |
| 2015/0119359 A1 | 4/2015 | Damireddi et al. |
| 2016/0220526 A1 | 8/2016 | Yuan et al. |
| 2016/0243057 A1 | 8/2016 | McWherter et al. |

FOREIGN PATENT DOCUMENTS

| CN | 104510732 A | 4/2015 |
| CN | 104720072 A | 6/2015 |
| CN | 106820118 A | 6/2017 |
| CN | 106924213 A | 7/2017 |
| KR | 10-2004-0062284 A | 7/2004 |
| WO | 2006/102236 A1 | 9/2006 |

OTHER PUBLICATIONS

Baenas N. et al., "Metabolic Activity of Radish Sprouts Derived Isothiocyanates in *Drosophila melanogaster*", International Journal of Molecular Sciences 17(2):251 (Feb. 18, 2016).
Tian G. et al., "The Stability and Degradation Kinetics of Sulforaphene in Microcapsules Based on Several Biopolymers Via Spray Drying", Carbohydrate Polymers 122:5-10 (Jan. 12, 2015).
Extended Supplementary European Search Report and Written Opinion dated Aug. 25, 2020 received in European Application No. 19 73 9191.5.
Barillari J. et al., "Kaiware Daikon (*Raphanus sativus* L.) Extract: A Naturally Multipotent Chemopreventive Agent", Journal of Agricultural and Food Chemistry 56:7823-7830 (2008).
Bhatia H. et al., "Traditional Phytoremedies for the Treatment of Menstrual Disorders in District Udhampur, J&K, India", Journal of Ethnopharmacology 160:202-210 (2015).
Choi K-C et al., "Intestinal Anti-Inflammatory Activity of the Seeds of *Raphanus sativus* L.in Experimental Ulcerative Colitis Models", Journal of Ethnopharmacology 179:55-65 (2016).
Kim M. et al., "The Ingredients in Saengshik, a Formulated Health Food, Inhibited the Activity of Alpha-Amylase and Alpha-Glucosidase as Anti-Diabetic Function", Nutrition Research and Practice 8(5)602-606 (2014).
Kook S-H et al., "*Raphanus sativus* L. Seeds Prevent LPS-Stimulated Inflammatory Response Through Negative Regulation of the p38 MAPK-NF-κB Pathway", International Immunopharmacology 23:726-734 (2014).
International Search Report dated Apr. 12, 2019 received in International Application No. PCT/US19/17150.

*Primary Examiner* — Kevin E Weddington

(74) *Attorney, Agent, or Firm* — Hoffmann and Baron, LLP

(57) ABSTRACT

The present disclosure provides stabilized sulforaphene compositions and uses thereof. The compositions include a stabilized sulforaphene, such as sulforaphene-cyclodextrin complex, that increases the efficacy, biological activity and stability of isolated sulforaphene. The present disclosure also includes pharmaceutical and nutraceutical compositions and methods for the treatment of mitochondrial disorders and muscular disorders. In addition, methods for increasing ATP and/or FAD production in cells by the administration of a stabilized sulforaphene are provided.

10 Claims, 4 Drawing Sheets
(3 of 4 Drawing Sheet(s) Filed in Color)

A

B

METHODS FOR USING STABILIZED SULFORAPHENE

CROSS REFERENCE TO RELATED APPLICATIONS

This application is a continuation in-part of U.S. patent application Ser. No. 16/479,288 filed on Jul. 19, 2019, which is the national phase of PCT/US2019/017150 filed on Feb. 8, 2019, which claims benefit of U.S. Provisional Application No. claims priority from U.S. Provisional Application No. 62/628,353 filed on Feb. 9, 2018, the entire contents of each of which is incorporated herein by reference.

FIELD OF THE DISCLOSURE

The present disclosure provides compositions that include stable sulforaphene and uses thereof. Specifically, the present disclosure includes pharmaceutical and nutraceutical compositions for use in treating mitochondrial disorders and muscular disorders. More specifically, the present disclosure relates to methods for treating subjects having a mitochondrial disorder by administering a pharmaceutical or nutraceutical composition including a stable sulforaphene. The present disclosure also provides methods for treating subjects having a muscular disorder by administering a pharmaceutical or nutraceutical composition including a stable sulforaphene. The present disclosure also provides methods for increasing ATP production and/or FAD levels in a cell.

BACKGROUND OF THE DISCLOSURE

Certain components found in the seeds of Brassicaceae family of vegetables such as, for example, radish (*Raphamus sativus*) are known to have anti-cancer activity and anti-microbial properties. See PCT/US2006/010032. One such component, sulforaphane is present in such plants in bound form as glucoraphanin, a glucosinolate. In nature, sulforaphane, $C_6H_{11}NOS_2$, which has the following chemical structure:

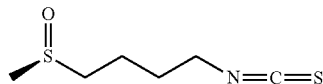

is formed from glucoraphanin following an enzymatic reaction. However, while many studies have focused on the isolation and use of sulforaphane, other components such as sulforaphene have been overlooked due to their lack of solubility, bioavailability and lack of stability after isolation.

Mitochondrial disorders are the diseases or defects that occur when mitochondria are unable to produce adenosine 5-triphosphate (ATP) by oxidative phosphorylation. Mitochondria are essential organelles present in all mammalian cells. Briefly, mitochondria generate ATP from adenosine diphosphate (ADP) during cellular respiration by transferring electrons from NADH or $FADH_2$ to $O_2$ through electron carriers, a process known as the electron transport train. Here, the energy released when electrons are passed from higher-energy NADH or $FADH_2$ to the lower-energy $O_2$ is required to phosphorylate ADP and generate ATP. The energy used to generate ATP from ADP is governed by the electron transport chain and is generated by oxidative phosphorylation. The electron transport chain is essential for producing cellular energy and maintaining cellular viability. Therefore, dysfunction in the electron transport chain of mitochondria results in a reduction of cellular ATP production, an increase in anaerobic metabolism, and increase in free radical production leading to oxidative stress and cell death.

Flavin adeniune dinucleotide (FAD)-dependent proteins function in a large variety of metabolic pathways including electron transport within the matrix of mitochondria. For example, during the citric acid cycle (i.e., TCA or Krebs cycle), succinate dehydrogenase requires covalently bound FAD to catalyze the oxidation of succinate to fumarate by coupling it with the reduction of ubiquinone to ubiquinol. See Kim et al. Biochimica et Biophysica Acta. (2013) Vol. 1827(5) pp. 627-36. The high-energy electrons from this oxidation are stored momentarily by reducing FAD to $FADH_2$. $FADH_2$ then reverts to FAD, sending its two electrons through the electron transport chain to produce ATP by oxidative phosphorylation. See Stryer L. et al., *Biochemistry* 6th ed. (2007) New York: Freeman.

Mitochondrial disorders can include one or more associated conditions, such as aberrant: mitochondrial oxidative metabolism, aerobic metabolism, muscle weakness, fatigue, heart failure or malfunction, limited mobility and seizures. Furthermore, Mitochondrial disorders also include FAD mediated disorders, such as muscular disorders (e.g., mitochondrial myopathy).

Considering the drawbacks associated with the existing treatments and the increasing number of patients diagnosed with mitochondrial and muscular disorders, there is a need to develop new compositions and methods for the treatment thereof.

SUMMARY OF THE DISCLOSURE

The methods and compositions of the present disclosure are based, in part, on the discovery that sulforaphene, when isolated from radish seeds, is a highly unstable but effective compound for the treatment of certain disorders. More specifically, the inventor has discovered that the efficacy and bioavailability of sulforaphene is severely diminished mere days after isolation. A finding which eliminates any potential therapeutic uses for sulforaphene. However, the inventor also discovered that compositions composed of stable sulforaphene prolongs the bioactivity of sulforaphene and significantly improves sulforaphene's ability to treat mitochondrial disorders through sulforaphene's activity as a redox cofactor, resulting in an increase in cellular ATP production.

As such, one aspect of the present disclosure provides a method for treating a mitochondrial disorder that includes administering to a subject a pharmaceutical or nutraceutical composition composed of a stabilized sulforaphene. In one instance, the present disclosure provides a method for increasing mitochondrial function by increasing a cells production of ATP through the administration of a composition composed of a stabilized sulforaphene to a subject. Here, sulforaphene functions as a redox co-factor that, acts to increase electron transport in the mitochondria and increase ATP production in a cell.

This methods of the present disclosure include the use a pharmaceutical or nutraceutical composition comprising stabilized sulforaphene. In some embodiments, the stabilized sulforaphene may be chemically modified to improve solubility of the sulforaphene compound. In other embodiments, the sulforaphene may be stabilized by the presence of one or more solubilizing agents in the pharmaceutical or nutraceutical composition. In one embodiment, the stabilizing agent is a cyclodextrin, an alcohol, a glycol, a ketone, an oil, or a combination thereof.

In some embodiments, the pharmaceutical or nutraceutical composition includes sulforaphene and a cyclodextrin. In certain embodiments, the cyclodextrin is one or more of an alpha cyclodextrin, a beta cyclodextrin, or a gamma cyclodextrin.

In a preferred embodiment, the pharmaceutical or nutraceutical composition includes sulforaphene and hydroxypropyl-beta-cyclodextrin. Therefore, in a specific embodiment, the present method includes administering to a subject a pharmaceutical composition that includes complex of a sulforaphene and a hydroxypropyl-beta-cyclodextrin (i.e., a stabilized sulforaphene).

In one embodiment, the pharmaceutical or nutraceutical composition consists essentially of a stabilized sulforaphene. In other embodiments, the composition consists essentially of a sulforaphene complexted with a cyclodextrin, such as hydroxypropyl-beta-cyclodextrin.

In some instances, the present disclosure is directed to methods including administering a pharmaceutical or nutraceutical composition to a subject. Administration can, for example, be oral, intravenous, intraperitoneal or topical. In a specific embodiment, the subject is orally administered a pharmaceutical or nutraceutical composition that contains a stable sulforaphene composition. In other embodiments, the composition is administered to the subject by injection, such as by intravenous or intraperitoneal injection. In certain embodiments, the composition is orally administered as a pill, liquid, powder or combination thereof.

In some embodiments, the subject being treated by the present methods is a mammal. In certain embodiments, the subject is a human, mouse or rat. In one exemplary embodiment, the subject being treated is a human subject having a mitochondrial disorder. In one instance, the subject being treated may exhibit a reduction in mitochondrial function such as ATP production. In a specific embodiment, the subject is a human that has been diagnosed with a mitochondrial disorder, whereby the mitochondrial disorder affects the ability of the subject to produce ATP by mitochondrial oxidative phosphorylation. Mitochondrial disorders can include one or more associated conditions, such as aberrant: mitochondrial oxidative metabolism, aerobic metabolism, muscle weakness, fatigue, heart failure or malfunction, limited mobility and seizures.

Exemplary mitochondrial disorders that can be treated by the present methods include, but are not limited to, mitochondrial myopathy, essential tremor, Parkinson's disease, metabolic disorders that result in aberrant metabolism of carbohydrates, lipids (fats), proteins, and/or nucleic acids by a subject such as mitochondrial diabetes, chronic fatigue syndrome (CFS), skin aging, prostatic disease (e.g., benign prostatic hyperplasia (BPH)), hyperthyroidism, glucose intolerance, hypercholesterolemia, dyslipidemia, hyperinsulinemia, thyroid dysfunction, multiple sclerosis, polycystic ovary syndrome (PCOS), psoriasis and coronary artery disease.

In one embodiment, the mitochondrial disorder being treated by administration of solubilized sulforaphene is mitochondrial myopathy. In a specific embodiment, the method of the present disclosure includes orally administering to a subject diagnosed with mitochondrial myopathy an effective amount of a pharmaceutical or nutraceutical composition that includes complex of a sulforaphene and a hydroxypropyl-beta-cyclodextrin.

In other embodiments, the method of the present disclosure includes administering to a subject diagnosed with essential tremor, an effective amount of a pharmaceutical composition that includes complex of a sulforaphene and a hydroxypropyl-beta-cyclodextrin.

In another embodiment, the method of the present disclosure includes orally administering to a subject diagnosed with polycystic ovary syndrome (PCOS), an effective amount of a pharmaceutical composition that includes complex of a sulforaphene and a hydroxypropyl-beta-cyclodextrin In other embodiments, the method of the present disclosure includes orally administering to a subject diagnosed with a skin disorder, such as psoriasis, an effective amount of a pharmaceutical composition that includes complex of a sulforaphene and a hydroxypropyl-beta-cyclodextrin. In one instance, the method of the present disclosure is used to treat subject having psoriatic arthritis, or skin aging by administration of an effective amount of a pharmaceutical composition that includes complex of a sulforaphene and a hydroxypropyl-beta-cyclodextrin.

In other embodiments, the method of the present disclosure includes orally administering to a subject diagnosed with chronic fatigue syndrome (CFS) an effective amount of a pharmaceutical composition that includes complex of a sulforaphene and a hydroxypropyl-beta-cyclodextrin.

In addition, the inventor has discovered that compositions composed of stable sulforaphene prolongs the bioactivity of sulforaphene and significantly improves a muscle cell's ability to produce FAD through sulforaphene's redox cofactor action. For example, surprisingly, it has been shown that administration of greater than 2 µg/mL of a stable sulforaphene results in a significant increase in the amount of FAD produced by muscles cells when compared to both negative controls and cells that have been administered 2 µg/mL or less of stabilized sulforaphene. Therefore, since FAD is used by the mitochondria to produce energy (i.e, ATP), the Inventor has discovered that the administration of specific amounts of a stable sulforaphene composition can treat FAD-mediated muscular disorders by increasing the levels of FAD present in a muscle cell.

As such, one aspect of the present disclosure provides a method for increasing the levels of FAD in a cell that includes administering to the cell a stabilized sulphoraphene, and detecting the level of FAD in the cell. In certain instances, the stabilized sulphoraphene is a sulforaphene and hydroxypropyl-beta-cyclodextrin complex.

In certain embodiments, the present disclosure provides a method for increasing FAD in a muscle cell by the administration of greater than 2 µg/mL of a stabilized sulforaphene.

The foregoing stabilized sulforaphene compositions can be formed and administered as provided herein.

In some embodiments, the stabilized sulforaphene comprises a sulforaphene and hydroxypropyl-beta-cyclodextrin complex. In one embodiment, the stabilized sulforaphene consists essentially of greater than 2 µg/mL of a sulforaphene and hydroxypropyl-beta-cyclodextrin complex. In another embodiment, the stabilized sulforaphene consists of greater than 2 µg/mL of a sulforaphene and hydroxypropyl-beta-cyclodextrin complex. In one embodiment, the stabilized sulforaphene consists essentially of greater than 2 µg/mL to 17.5 µg/mL. In another embodiment, the stabilized sulforaphene comprises between 2.1 µg/mL and 17.5 µg/mL of a sulforaphene and hydroxypropyl-beta-cyclodextrin complex. In yet another embodiment, the stabilized sulforaphene consists essentially of between 2.1 µg/mL and 17.5

µg/mL of a sulforaphene and hydroxypropyl-beta-cyclodextrin complex. In other embodiments, the stabilized sulforaphene comprises 17.5 µg/mL of a sulforaphene and hydroxypropyl-beta-cyclodextrin complex. In one embodiment, the stabilized sulforaphene consists essentially of 17.5 µg/mL of a sulforaphene and hydroxypropyl-beta-cyclodextrin complex.

In certain embodiments the level of FAD in a cell can be detected by fluorometric or colormetric methods.

In yet another aspect of the present disclosure, a method for treating a muscular disorder that includes administering to a subject a greater than 2 µg/mL of a stabilized sulforaphene. In one instance, the present disclosure provides a method for increasing muscle function by the administration of greater than 2 µg/mL of a stabilized sulforaphene.

In certain instances, the stabilized sulforaphene can be included within a pharmaceutical or nutraceutical composition composed of a stabilized sulforaphene.

The foregoing stabilized sulforaphene compositions can be formed and administered as provided herein.

In some embodiments, the stabilized sulforaphene comprises a sulforaphene and hydroxypropyl-beta-cyclodextrin complex. In one embodiment, the stabilized sulforaphene consists essentially of greater than 2 µg/mL of a sulforaphene and hydroxypropyl-beta-cyclodextrin complex. In another embodiment, the stabilized sulforaphene consists of greater than 2 µg/mL of a sulforaphene and hydroxypropyl-beta-cyclodextrin complex. In one embodiment, the stabilized sulforaphene consists essentially of greater than 2 g/mL to 17.5 µg/mL. In another embodiment, the stabilized sulforaphene comprises between 2.1 µg/mL and 17.5 µg/mL of a sulforaphene and hydroxypropyl-beta-cyclodextrin complex. In yet another embodiment, the stabilized sulforaphene consists essentially of between 2.1 µg/mL and 17.5 µg/mL of a sulforaphene and hydroxypropyl-beta-cyclodextrin complex. In other embodiments, the stabilized sulforaphene comprises 17.5 µg/mL of a sulforaphene and hydroxypropyl-beta-cyclodextrin complex. In one embodiment, the stabilized sulforaphene consists essentially of 17.5 µg/mL of a sulforaphene and hydroxypropyl-beta-cyclodextrin complex.

In some embodiments, the subject being treated by the present methods is a mammal. In certain embodiments, the subject is a human, mouse or rat. In one exemplary embodiment, the subject being treated is a human subject having a muscular disorder. In one instance, the subject being treated may exhibit a reduction in ATP and/or FAD production. In a specific embodiment, the subject is a human that has been diagnosed with a muscular disorder, whereby the muscular disorder affects the ability of the subject to produce FAD in muscle cells. Muscular disorders can include one or more associated conditions, such as aberrant: oxidative metabolism, aerobic metabolism, muscle weakness, fatigue, heart failure or malfunction, limited mobility and seizures.

Exemplary muscular disorders that can be treated by the present methods include, but are not limited to, mitochondrial myopathy, essential tremor, Parkinson's disease, chronic fatigue syndrome (CFS), amyotrophic lateral sclerosis (ALS), multiple sclerosis, muscular dystrophy, and myopathy.

In one embodiment, the muscular disorder being treated by administration of solubilized sulforaphene is mitochondrial myopathy. In a specific embodiment, the method of the present disclosure includes orally administering to a subject diagnosed with mitochondrial myopathy an effective amount of a pharmaceutical or nutraceutical composition that includes complex of a sulforaphene and a hydroxypropyl-beta-cyclodextrin. In another embodiment, the subject having mitochondrial myopathy is administered the composition by injection. In a specific embodiment, the injection is by intrapertoneal injection to the muscle cells.

In other embodiments, the method of the present disclosure includes administering to a subject diagnosed with essential tremor, an effective amount of a composition that includes complex of a sulforaphene and a hydroxypropyl-beta-cyclodextrin.

In another embodiment, the method of the present disclosure includes administering to a subject diagnosed with muscular distrophy, an effective amount of a composition that includes complex of a sulforaphene and a hydroxypropyl-beta-cyclodextrin.

In other embodiments, the method of the present disclosure includes administering to a subject diagnosed with chronic fatigue syndrome (CFS) an effective amount of a pharmaceutical composition that includes a complex of a sulforaphene and a hydroxypropyl-beta-cyclodextrin.

BRIEF DESCRIPTION OF THE DRAWINGS

The patent or application file contains at least one drawing executed in color. Copies of this patent or patent application publication with color drawings will be provided by the office upon request and payment of the necessary fee.

DETAILED DESCRIPTION OF THE DISCLOSURE

Figure 1A:
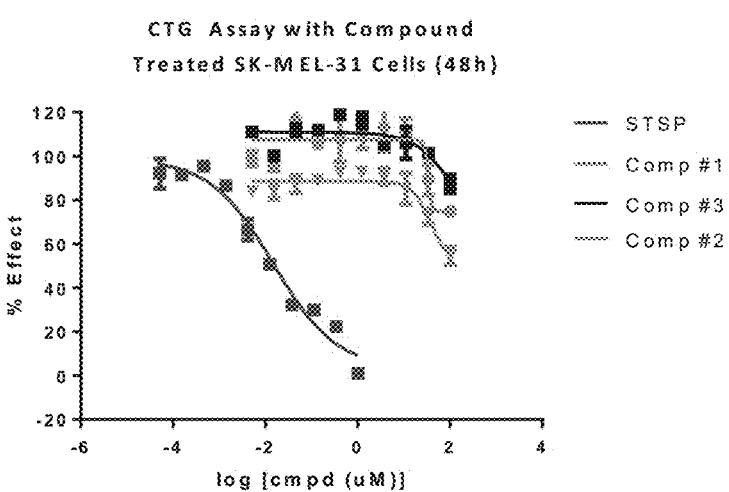
FIGS. 1A-1B. Stabilized sulforaphene induces mitochondrial ATP production in skin cells. SK-MEL-31 human skin cells were cultured and plated in 96-well plates at a cell density of 15,000 cells per well. Cells were then treated with staurosporine (STSP), a known inhibitor of mitochondrial function and ATP production. After incubation with STSP, cells were then administered either 100 µM of a sulforaphene and hydroxypropyl-beta-cyclodextrin complex (compound 1), 17.5 µg/µL of a stabilized sulforaphene composition isolated from radish seed extract (compound 2) or 17.5 µg/µL of a positive control known to induce ATP production (compound 3). Cells were then incubated for 4 hours (data not shown), 48 hours (A) or 72 hours (B). Skin cells treated with stabilized sulforaphene compositions for more than 4 hours exhibited an increase in mitochondrial function similar to that of cells treated with a positive control and significantly above that of cells treated with STSP alone.

Without being bound by any one particular theory, the inventive methods are based, in part, on the discovery that sulforaphene becomes unstable and ineffective shortly after isolation of the sulforaphene compound from the Brassicaceae family of plants, such as *Raphanus sativus* (radish) in which sulforaphene naturally forms. Furthermore, the Inventor has discovered that stabilization of sulforaphene is the active compound in radish seed extract for the treatment of certain disorders. For example, as shown herein, stabilized sulphoraphene improves mitochondrial ATP production through its activity as a redox co-factor, when compared to radish seed extracts, which results in increased cell viability and maintenance. In another example, the Inventor has discovered that stabilized sulforaphene increases the level of flavin adenine dinucleotide (FAD) in muscle cells. Therefore, the present disclosure also includes methods for treating a subject with a muscular disorder.

In one aspect of the present disclosure, the inventor determined that pharmaceutical and nutraceutical compositions composed of stabilized sulforaphene, such as sulforaphene complexed with hydroxypropyl-beta-cyclodextrin, prolongs the bioactivity of sulforaphene and significantly improves the ability of sulforaphene to treat mitochondrial disorders such as, for example, mitochondrial myopathy (e.g., chronic fatigue syndrome (CFS)), essential tremor, mitochondrial diabetes, PCOS, and skin disorders (e.g., psoriasis and aging skin).

Therefore, the present disclosure provides a method for treating a mitochondrial disorder that includes administering a pharmaceutical or nutraceutical composition composed of stabilized sulforaphene to a subject.

In another aspect of the present disclosure, a method for treating a muscular disorder is provided. Here, it has been shown that administering greater than 2 µg/mL of a stabilized sulforaphene to a subject increased the amount of FAD produced by human muscle cells. Therefore, the present disclosure provides a method for increasing muscle function in a subject by the administration of greater than 2 µg/mL of a stabilized sulforaphene.

In certain instances, the stabilized sulforaphene can be included within a pharmaceutical or nutraceutical composition composed of a stabilized sulforaphene.

The therapeutic methods of the present disclosure include the administration of a pharmaceutical or nutraceutical composition that includes stabilized sulforaphene. The term "sulforaphene" or "raphanin" as used herein shall mean the chemical compound having a molecular formula of $C_6H_9NOS_2$, and the following structure:

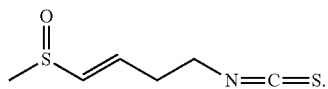

Sulforaphene has several known aliases, such as sulforaphen, sulphoraphen, 4-isothiocyanato-1-(methylsulfinyl)-1-butene, 4-methylsufinyl-3-butenyl isothiocyanate. Sulforphene has a known molecular weight of approximately 175.26 g/mol. Sulforaphene as used herein is not intended to include sulforaphane, which has a structure and activity distinct from that of sulforaphene. As stated above, sulforaphane has a molecular formula of $C_6H_{11}NOS_2$, which, for example, lacks a double bond between the first and second carbon of the molecule also known as 1-isothiocyanato-4-[(R)-methylsulfinyl]-butane.

Sulforaphene, unlike sulforaphene, is a vinylic sulfoxide redox cofactor, generally having the structural formula R—S(=O)—R' which play a role as Michael acceptors in organic chemistry. Vinylic sulfoxides are chemical compounds that modulate anaerobic oxidative phosphorylation in the mitochondria. Redox cofactors catalyze redox reactions, such as those present in the electron transport chairs and can result in an increase in ATP production. Redox cofactors have been known to play a role in inflammation and infection.

Sulforaphene is a naturally occurring compound found, for example, in the seeds of radishes (*Raphani semen*) that is created by hydrolysis of glucoraphenin (a glucosinolate) by myrosinase. Therefore, in certain embodiments, sulforaphene can be isolated from certain root vegetables, such as radish. Isolated naturally occurring sulforaphene can also be purified for use in the present methods.

The term "isolated", when used in reference to a compound such as sulforaphene means that the compound has been removed from its naturally occurring environment or the environment from which it was formed and is substantially free of other molecules material. By "substantially free", it is meant that isolated compound accounts for at least 60%, 70%, 80%, 90%, or 95% (by dry weight or volume) of a composition or preparation. For example, an isolated sulforaphene composition can be substantially free from other compounds (proteins, lipids, collagen) or materials of the plant from which it was obtained, i.e., sulforaphene represents more than about 80% of the volume of the preparation, more than about 90% of the volume of the preparation or more than about 95% of the volume of the preparation. The level of purification can be based on the intended use.

Methods for isolating and purifying sulforaphene from radish seeds are known by those of ordinary skill the art, and any such method can be used here. For example, radish seeds may be defatted prior to forming an aqueous extract using known defatting procedures such as those set forth in West, L. et al., *J Agric. Food Chem.* (2004) 52, pp. 916-926 the entire contents of which is hereby incorporated by reference. Here, the plant or a portion thereof may be ground, pulverized or blended prior to addition of aqueous extract or simultaneously with the addition of an aqueous extract. Extraction of sulforaphene may be conducted with water or water containing an organic solvent, such as ethyl alcohol. Specifically, in some instances, an aqueous extract of crucifer plants is formed by contacting crucifer seeds with water having a temperature of 60 to 110° C. for at least 5 minutes. The aqueous extract can then be contacted with an adsorbent that preferentially adsorbs to sulforaphene instead of other compounds in the extract, such as activated carbon, silica, chemically-modified silica, bleaching clay and the like as well as and mixtures thereof. Once the desired compound is adsorbed it can be isolated from highly molecular weight proteins or compounds.

In other embodiments, the sulforaphene can be synthetically produced such as, for example, clink chemistry, combinatory chemistry, cycloaddition reactions or solid-phase synthesis. However, other known methods for forming synthetic sulforaphene will be readily known by those of skill in the art.

As stated above, the pharmaceutical or nutraceutical composition of the present disclosure includes "stabilized sulforaphene". As used herein, "stabilized sulforaphene" or "stable sulforaphene" are used interchangeably herein to mean a sulforaphene compound or sulforaphene containing compound (e.g., complex) that is more bioactive than naturally isolated sulforaphene over time. Bioactivity can be determined by methods known by those of ordinary skill in the art, such as cell culture assays, in vivo studies, receptor binding assays, spectrophotometry and more. In certain instances, sulforaphene is stabilized by altering the chemical structure by known methods, such as for example, modifying a side group, modifying the charge of the molecule, or adding a methyl group. In other instances the sulforaphene is stabilized through the use of a stabilizing agent.

The term "agent" as used herein refers to any kind of composition or combination of compositions. In one embodiment of the present disclosure the agent is a small molecule. In another embodiment of the disclosure, the agent is a biological molecule, including, but not limited to, a protein, a polypeptide, an antibody or a nucleic acid. In certain embodiments, the stabilizing agent is a cyclodextrin, an alcohol, a glycol, a ketone, an oil, or a combination thereof. In specific embodiments, the stabilized sulforphene includes a complex of a sulforaphene and a stabilizing agent. In one exemplary embodiment, the stabilizing agent is hydroxypropyl-beta cyclodextrin.

In some embodiments, the composition includes a stabilized sulforaphene is a sulforaphene/cyclodextrin complex. The cyclodextrin can be one or more of an alpha cyclodextrin, a beta cyclodextrin, a gamma cyclodextrin, or a hydroxyalkyl derivative thereof.

In a specific embodiment, the composition includes stabilized sulforaphene selected from one or more of the following sulforaphene/cyclodextrin complexes: sulforaphene and a beta cyclodextrin, or a hydroxyalkyl derivative thereof.

In one embodiment, a pharmaceutical or nutraceutical composition can consist essentially of a stabilized sulforaphene, which shall mean that the only essential element of the composition is stabilized sulforaphene (i.e., the active agent). In other embodiments, the pharmaceutical composition consists essentially of a stabilized sulforaphene, whereby the stabilized sulforaphene is sulforaphene complexed with a cyclodextrin or hydroxyalkyl derivative thereof, which shall mean that the only essential elements of the composition are sulforaphene (i.e., the active agent) and cyclodextrin.

In yet other embodiments, the composition consists essentially of a stabilized sulforaphene, whereby the stabilized sulforaphene is sulforaphene complexed with a beta cyclodextrin or hydroxyalkyl derivative thereof, which shall mean that the only essential elements of the composition are sulforaphene (i.e., the active agent) and beta cyclodextrin. While these pharmaceutical compositions may include other elements, such as additives or solvents, such other elements may be readily substituted for other similar or like elements.

In one exemplary embodiment, the pharmaceutical or nutraceutical composition includes a stabilized sulforaphene/cyclodextrin complex consisting of hydroxypropyl-beta cyclodextrin and sulforaphene.

In some embodiments, the stabilized sulforaphene consists essentially of greater than 2 µg/mL of a sulforaphene and hydroxypropyl-beta-cyclodextrin complex. In another embodiment, the stabilized sulforaphene consists of greater than 2 µg/mL of a sulforaphene and hydroxypropyl-beta-cyclodextrin complex. In one embodiment, the stabilized sulforaphene consists essentially of greater than 2 µg/mL to 17.5 µg/mL. In another embodiment, the stabilized sulforaphene comprises between 2.1 µg/mL and 17.5 µg/mL of a sulforaphene and hydroxypropyl-beta-cyclodextrin complex. In yet another embodiment, the stabilized sulforaphene consists essentially of between 2.1 µg/mL and 17.5 µg/mL of a sulforaphene and hydroxypropyl-beta-cyclodextrin complex. In other embodiments, the stabilized sulforaphene comprises 17.5 µg/mL of a sulforaphene and hydroxypropyl-beta-cyclodextrin complex. In one embodiment, the stabilized sulforaphene consists essentially of 17.5 µg/mL of a sulforaphene and hydroxypropyl-beta-cyclodextrin complex.

In specific embodiments, the stabilized sulforaphene comprises 2.1 µg/mL, 2.5 µg/mL, 3.0 µg/mL, 3.5 µg/mL, 4.0 µg/mL, 4.5 µg/mL, 5.0 µg/mL, 5.5 µg/mL, 6.0 µg/mL, 6.5 µg/mL, 7.0 µg/mL, 7.5 µg/mL, 8.0 µg/mL, 8.5 µg/mL, 9.0 µg/mL, 9.5 µg/mL, 10.0 µg/mL, 10.5 µg/mL, 11.0 µg/mL, 11.5 µg/mL, 12.0 µg/mL, 12.5 µg/mL, 13.0 µg/mL, 13.5 µg/mL, 14.0 µg/mL, 14.5 µg/mL, 15.0 µg/mL, 15.5 µg/mL, 16.0 µg/mL, 16.5 µg/mL, 17.0 µg/mL, 17.5 µg/mL, or greater of a sulforaphene and hydroxypropyl-beta-cyclodextrin complex.

In some embodiments, the present methods utilize a pharmaceutical or nutraceutical composition that includes stabilized sulforaphene that is greater than 75% pure sulforaphene, greater than 80% pure sulforaphene, greater than 85% pure sulforaphene, greater than 90% pure sulforaphene, greater than 95% pure sulforaphene or greater than 99% sulforaphene. In some instances, the ratio of molar ratio of stable sulforaphene to other elements of the pharmaceutical composition is within the range of 0.3:1, 0.4:1, 0.5:1, 0.6:1, 0.7:1, 0.8:1, 0.9:1 or greater.

The pharmaceutical or nutraceutical composition including a stabilized sulforaphene and cylcodextrin can be formed by mixing the sulforaphene or the natural source thereof with a cyclodextrin in a suitable solvent to form a precipitate. Any suitable solvent known in the art may be utilized. In certain instances, the solvent is an aqueous solvent comprising water and optionally one or more water-miscible solvents, such as ethanol. In other instances the solvent is water. The dissolution of cyclodextrin in solvent may be accomplished by any dissolution method known in the art.

For example, the cyclodextrin may be fully or partially dissolved in a solvent by placing cyclodextrin in the solvent and heating the mixture. In another example, sonication may be utilized to either fully or partially dissolve the cyclodextrin in the solvent. Once the sulforaphene and cyclodextrin have been combined in solution they can be mixed and cooled to form a precipitate (stabilized sulforaphene). The precipitate may then be filtered to obtain a stable sulforaphene-cyclodextrin complex.

In some embodiments, the present methods utilize a pharmaceutical composition that includes sulforaphene within the cyclodextrin complex being greater than 75% pure sulforaphene, greater than 80% pure sulforaphene, greater than 85% pure sulforaphene, greater than 90% pure sulforaphene, greater than 95% pure sulforaphene or greater than 99% sulforaphene. In some instances the ratio of molar ratio of sulforaphene to cyclodextrin in the resultant complex is within the range of 0.3:1, 0.4:1, 0.5:1, 0.6:1, 0.7:1, 0.8:1, 0.9: or greater. In specific instances, the ratio of sulforphene to cyclodextrin is 0.8:1 to 1:1, 0.9:1-1:1, 0.95:1 to 1:1 or 0.98:1 to 1:1.

In some embodiments, the pharmaceutical composition is formulated as a unit-dose composition, for example, a tablet, powder or liquid, which can contain from about 0.1% to 100%, 0.1% to 90%, 0.1% to 80%, 0.1% to 70%, 0.1% to 60%, 0.1% to 50%, 0.1% to 40%, 0.1% to 30%, 0.1% to 20% or 0.1% to 10% by weight of the active compound, i.e., stabilized sulforaphene. In one embodiment, the pharmaceutical composition contains 5.0% to 30%, 10% to 25% or 10% to 20% by weight of stabilized sulforaphene. In a specific embodiment, the pharmaceutical composition contains 10% to 22% by weight of stabilized sulforaphene.

In some embodiments, the stabilized sulforaphene comprises a pharmaceutical or nutraceutical composition that includes sulforaphene and hydroxypropyl-beta-cyclodextrin complex. In one embodiment, the pharmaceutical or nutraceutical composition consists essentially of greater than 2 µg/mL of a sulforaphene and hydroxypropyl-beta-cyclodextrin complex. In another embodiment, the pharmaceutical or nutraceutical composition consists of greater than 2 µg/mL of a sulforaphene and hydroxypropyl-beta-cyclodextrin complex. In another embodiment, the pharmaceutical or nutraceutical composition comprises between 2.1 µg/mL and 17.5 µg/mL of a sulforaphene and hydroxypropyl-beta-cyclodextrin complex. In yet another embodiment, the pharmaceutical or nutraceutical composition consists essentially of between 2.1 µg/mL and 17.5 µg/mL of a sulforaphene and hydroxypropyl-beta-cyclodextrin complex. In other embodiments, the pharmaceutical or nutraceutical composition comprises 17.5 µg/mL of a sulforaphene and hydroxypropyl-beta-cyclodextrine complex. In one embodiment, the pharmaceutical or nutraceutical composition consists essentially of 17.5 µg/mL of a sulforaphene and hydroxypropyl-beta-cyclodextrin complex.

In some embodiments the pharmaceutical or nutraceutical composition comprises 2.1 µg/mL, 2.5 µg/mL, 3.0 µg/mL, 3.5 µg/mL, 4.0 µg/mL, 4.5 µg/mL, 5.0 µg/mL, 5.5 µg/mL, 6.0 µg/mL, 6.5 µg/mL, 7.0 µg/mL, 7.5 µg/mL, 8.0 µg/mL, 8.5 µg/mL, 9.0 µg/mL 9.5 µg/mL, 10.0 µg/mL, 10.5 µg/mL, 11.0 µg/mL, 11.5 µg/mL, 12.0 µg/mL, 12.5 µg/mL, 13.0 µg/mL, 13.5 µg/mL, 14.0 µg/mL, 14.5 µg/mL, 15.0 µg/mL, 15.5 µg/mL, 16.0 µg/mL, 16.5 µg/mL, 17.0 µg/mL, 17.5 µg/mL, or greater of a sulforaphene and hydroxypropyl-beta-cyclodextrin complex In certain non-limiting embodiments, the pharmaceutical or nutraceutical compositions of the present disclosure include a stabilized sulforaphene and at least one additive. In specific embodiments, the pharmaceutical composition includes a stabilized sulforaphene/cyclodextrin complex and at least one additive. Additives can include carriers, stabilizers, anti-oxidants, colorants, diluents and excipients that do not alter the performance of sulforaphene to such an extent that treatment is ineffective.

Exemplary carriers include, but are not limited to, physiological saline, Ringer's, phosphate solution or buffer, buffered saline, and other carriers known in the art. The carrier can be a solid or a liquid, or both, and may be formulated with the pharmaceutical composition as a unit-dose composition, for example, a tablet, powder or liquid, which can contain from about 0.1% to 100%, 0.1% to 90%, 0.1% to 80%, 0.1% to 70%, 0.1% to 60%, 0.1% to 50%, 0.1% to 40%, 0.1% to 30%, 0.1% to 20% or 0.1% to 10% by weight of the active compound, i.e., stabilized sulforaphene. In one embodiment, the pharmaceutical composition contains 5.0% to 30%, 10% to 25% or 10% to 20% by weight of stabilized sulforaphene. In a specific embodiment, the pharmaceutical composition contains 10% to 22% by weight of stabilized sulforaphene.

A pharmaceutical or nutraceutical composition can be formulated on the basis of the desired route of administration of the stabilized sulforaphene. The desired route of administration may be one or more of oral, enteral, parenteral, injectable, buccal, and topical. For example, in an embodiment, a composition is suitable for oral administration. In some embodiments, the composition includes a carrier and/or additive(s) that is suitable for promoting delivery of the composition to the skin, gut or blood stream of a subject.

In particular, the pharmaceutical or nutraceutical compositions of the present disclosure, or formulations in which they are included, can be administered orally, for example, as tablets, coated tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more additives selected from the group consisting of sweetening agents, flavoring agents, coloring agents and preserving agents in order to provide pharmaceutically acceptable and palatable preparations.

Tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed.

Pharmaceutical or nutraceutical compositions of the present disclosure may also contain non-toxic excipients. These excipients may be, for example, inert diluents, such as calcium carbonate, sodium carbonate, lactose, calcium phosphate or sodium phosphate; granulating and disintegrating agents, for example, maize starch or alginic acid; binding agents, for example starch, gelatin, or acacia, and lubricating agents, for example magnesium stearate, stearic acid or talc.

Pharmaceutical or nutraceutical compositions may also be formulated as hard gelatin capsules wherein the active ingredients (stabilized sulforaphene, e.g., sulforphene/cyclodextrin complex) are mixed with an inert solid diluent, such as for example calcium carbonate, calcium phosphate or kaolin, or as soft gelatin capsules wherein the active ingredients are present or mixed with water or oil medium, such as for example peanut oil, liquid paraffin, any of a variety of herbal extracts, milk, or olive oil.

Aqueous suspensions can be produced that contain the active ingredients (stabilized sulforphene) in admixture with excipients suitable for the manufacture of aqueous suspensions. Such excipients include suspending agents, such as for example sodium carboxymethylcellulose, methylcellulose, hydroxypropylmethyl-cellulose, sodium alginate, polyvinylpyrrolidone gum tragacanth and gum acacia; dispersing or wetting agents may be naturally-occurring phosphatides, such as for example lecithin, or condensation products of an alkylene oxide with fatty acids, such as for example polyoxyethylene stearate, or condensation products of ethylene oxide with long chain aliphatic alcohols, such as for example heptadecaethyleneoxycetanol, or condensation products of ethylene oxide with partial esters derived from fatty acids and a hexitol, such as for example polyoxyethylene sorbitol monooleate or condensation products of ethylene oxide with partial esters derived from fatty acids and hexitol anhydrides, such as for example polyoxyethylene sorbitan monooleate.

The aqueous suspensions may also contain one or more preservatives, such as for example ethyl or n-propyl p-hydroxybenzoate, one or more coloring additives, one or more flavoring additives, or one or more sweetening agents, such as sucrose, glycerol, sorbitol or saccharin.

Oily suspensions may be formulated by suspending the active ingredients (stabilized sulforaphene, e.g., sulforphene/cyclodextrin complex) in an omega-3 fatty acid, a vegetable oil, such as for example arachis oil, olive oil, sesame oil or coconut oil, or in a mineral oil such as liquid paraffin. The oily suspensions may contain a thickening additive, such as for example beeswax, hard paraffin or cetyl alcohol.

Sweetening additives, such as those set forth above, and flavoring agents may be added to provide a palatable oral preparation.

Dispersible powders and granules suitable for preparation of a pharmaceutical composition by the addition of water provide the active ingredients (stabilized sulforaphene in admixture with a dispersing or wetting agent, a suspending agent and one or more preservatives. Suitable dispersing or wetting agents and suspending agents are exemplified by those already mentioned above. Additional excipients, for example sweetening, flavoring and coloring agents, may also be present.

Syrups and elixirs containing the stable sulforaphene (e.g., sulforaphane/cyclodextrin complex) may be formulated with sweetening agents, such as for example glycerol, sorbitol, or sucrose. Such formulations may also contain a demulcent, a preservative, and/or flavoring and coloring agents. Liquid dosage forms for oral administration can include pharmaceutically acceptable emulsions, solutions, suspensions, syrups, and/or elixirs containing inert diluents commonly used in the art, such as water. Such compositions may also comprise adjuvants, such as wetting agents, emulsifying and/or suspending agents, and sweetening, flavoring, and/or perfuming agents.

Pharmaceutical or nutraceutical compositions suitable for oral administration can be presented in discrete units each containing a predetermined amount of stabilized sulforaphene to effect treatment; as a powder or granules; as a solution or a suspension in an aqueous or non-aqueous liquid; or as an oil-in-water or water-in-oil emulsion. As indicated, such compositions can be prepared by any suitable method of pharmacy, which may include the step of bringing into association the active ingredient (stabilized sulforaphene, e.g., sulforphene/cyclodextrin complex) and the carrier (which can constitute one or more additives).

For example, a tablet can be prepared by compressing or molding a powder or granules of the stabilized sulforaphene, optionally with one or more accessory ingredients. Compressed tablets can be prepared by compressing, in a suitable machine, the compound in a free-flowing form, such as a powder or granules optionally mixed with a binder, lubricant, inert diluent and/or surface active/dispersing agent(s). Molded tablets can be lade by molding, in a suitable machine, the powdered compound moistened with an inert liquid diluent.

A pharmaceutical or nutraceutical composition of the present disclosure may be coated or uncoated to delay disintegration and absorption in the gastrointestinal tract and thereby provide a delayed action over a longer period. For example, a time delay material such as glyceryl monostearate or glyceryl distearate may be employed.

The compositions for use in the present methods may be injectable. For example, the pharmaceutical composition can be a sterile injectable solution or suspension in a non-toxic parenterally acceptable diluent or solvent, such as for example a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed, including synthetic mono- or di-glycerides. In addition, n-3 polyunsaturated fatty acids may find use in the preparation of injectables.

Pharmaceutical and nutraceutical compositions can also include sterile aqueous preparations prepared by admixing the stable sulforaphene with water and rendering the resulting solution sterile and isotonic with the blood. Injectable pharmaceutical compositions according to the invention will generally contain from 5% to 40% w/w of stable sulforaphene.

The injectable compositions may also include saline, dextrose, or water as a suitable carrier. A suitable dose of stabilized sulforaphene, e.g., sulforaphene/cyclodextrin complex, is one that achieves relatively the same blood serum level as described above.

The pharmaceutical compositions of the present disclosure can also be topical preparations to the skin and may take the form of ointments, creams, lotions, pastes, gels, sprays, powders, jellies, collyriums, solutions, suspensions, aerosols, or oils. Carriers may be used and include petroleum jelly (e.g., Vaseline®), lanolin, polyethylene glycols, alcohols, and combinations of two or more thereof. The active ingredients (stabilized sulforaphene, e.g., sulforphene/cyclodextrin complex) are generally present at a concentration of from about 0.1% to 100%, 0.1% to 90%, 0.1% to 80%, 0.1% to 70%, 0.1% to 60%, 0.1% to 50%, 0.1% to 40%, 0.1% to 30%, 0.1% to 20% or 0.1% to 10% by weight of the active compound, i.e., stabilized sulforaphene. In one embodiment, the pharmaceutical composition contains 5.0% to 30%, 10% to 25% or 10% to 20% by weight of stabilized sulforaphene. In a specific embodiment, the pharmaceutical composition contains 10% to 22% by weight of stabilized sulforaphene.

The present pharmaceutical and nutraceutical compositions may also include safe and effective amounts of isotonicity agents, including, salts, such as sodium chloride, and/or non-electrolyte isotonicity agents such as sorbitol and mannitol.

The present pharmaceutical and nutraceutical compositions may also be enhanced by incorporation of a surfactant or co-solvent. Such co-solvents include polysorbate 20, 60, and 80, polyoxyethylene/polyoxypropylene surfactants (e.g., Pluronic F-68, F-84 and P-103, available from BASF®) or other agents known to those skilled in the art.

Such co-solvents may be employed at levels of from about 0.01% to about 2% by weight.

Effective formulations and administration procedures are well known in the art and are described in standard textbooks. See e.g. Gennaro, A. R., *Remington: The Science and Practice al Pharmacy,* 20$^{th}$ Edition, (Lippincott, Williams and Wilkins), 2000; Hoover, John E., *Remington Pharmaceutical Sciences*, Mack Publishing Co., Easton, Pa., 1975; Liberman, et al., Eds., *Pharmaceutical Dosage Forms*, Marcel Decker, New York, N.Y., 1980; and Kibbe, et al., Eds., *Handbook of Pharmaceutical Excipients* (3$^{rd}$ Ed.), American Pharmaceutical Association, Washington, 1999.

As stated above, in certain embodiments, the stabilized sulforaphene is included in a nutraceutical composition. A "nutraceutical composition" as used herein means a multi-agent composition whereby one agent is a stable sulforaphene, and the other agents can target one or more distinct biochemical pathways to provide multiple therapeutic effects to a subject.

In some embodiments, a nutraceutical composition includes a stable sulforaphene and at least one, at least two, at least three, at least four, at least five, or at least six or more agents from the following groups, whose members have a therapeutic effect for one or more mammalian conditions, such as a mitochondrial disorder. Group 1: minerals, vitamins, and dietary supplements; Group 2: herbal products such as, for example, garlic (allicin), ginger, echinacea, ginseng, liquorice, onion, senna, turmeric (curcumin) or a portion thereof; Group 3: dietary enzymes such as, for example, bromelain and papain; Group 4: fiber; Group 5: hydrolyzed proteins; Group 6: phytonutrients such as, for example, resveratrol; Group 7: Carotenoids such as, for example, lycopene; Group 8: Prebiotics and probiotics.

In another embodiment, the nutraceutical composition includes a stable sulforaphene and an active ingredient at least one of the above groups. In a specific embodiment, the nutraceutical composition includes a stable sulforaphene and an active ingredient at least one of the above groups and is provided as food additive such as a powder. In certain embodiments, the nutraceutical composition includes a sulforaphene/cylcodextrin complex and at least one active ingredient from at least one of the above groups. In one embodiment, the nutraceutical composition includes a stable sulforaphene and at least one active ingredient from each of the above groups.

The present methods include administering to a subject nutraceutical composition that includes a stabilized sulforaphene including, but not limited to, a sulforaphene/cyclodextrin complex. For instance, administering to a subject a nutraceutical composition composed of a sulforaphene/hydroxypropyl-beta-cyclodextrin complex.

Any method for preparing a nutraceutical formulation can be used in accordance with the present methods. In certain instances, methods for preparing the nutraceutical compositions of the present disclosure will be the same or substantially the same as those used to prepare a pharmaceutical composition. In one embodiment, the nutraceutical compositions of the present disclosure are prepared by the same methods used to prepare the pharmaceutical compositions above. It other embodiments, the nutraceutical compositions are formulated and administered according to the above methods. In yet another embodiment, the nutraceutical compositions of the present disclosure are prepared using a method known by those of ordinary skill in the art.

Methods of Treatment.

A "subject," used herein interchangeably with the term "patient," can be a human or any other mammal including, without limitation, a primate, rat, mouse, rabbit, pig, cow, sheep, goat, cat or dog. A "subject" as used herein, is any subject having a condition (direct, associated or otherwise) which, in the judgment of a practitioner (e.g., clinician or veterinarian), is indicative of a mitochondrial disorder or a muscular disorder.

In some embodiments, the subject being treated by the present methods is a mammal. In certain embodiments, the subject is a human, mouse or rat. In one exemplary embodiment, the subject being treated is a human subject having a condition which is indicative of a mitochondrial disorder. In a specific embodiment, the subject is a human that has been diagnosed with a mitochondrial disorder, whereby the mitochondrial disorder effects the ability of the subject to metabolize carbohydrates, lipids (fats), proteins, and/or nucleic acids and generate ATP.

In some instances, the subject has one or more of the following conditions associated with a mitochondrial disorder, such as aberrant: mitochondrial oxidative metabolism, reduced ATP production and/or reduced cellular viability.

In other embodiments, the subject being treated is a human subject having a condition which is indicative of a muscular disorder. In a specific embodiment, the subject is a human that has been diagnosed with a muscular disorder, whereby the disorder effects the ability of the subject to generate FAD in muscle cells.

Administration can, for example, be oral, intravenous, intraperitoneal or topical. In a specific embodiment, the subject is orally administered a stable sulforaphene composition. In other embodiments the composition is administered to the subject by injection, such as by intravenous or intraperitoneal injection. In another embodiment, the pharmaceutical composition is administered topically.

In a specific embodiment, the subject is administered the stabilized sulforaphene by injection directly to the affected tissue, such as muscle tissue.

In the present methods, a subject in need of treatment and/or prevention of one or more of the mitochondrial disorders or muscular disorders described herein or conditions thereof may be treated by administration of an amount of a pharmaceutical or nutraceutical composition composed of stable sulforaphene such that the amount of the active component(s) (stable sulforaphene, e.g., sulforaphene/cyclodextrin complex) provides a dosage or amount that is sufficient to constitute a treatment or prevention of the disorder or a symptom thereof (i.e., an "effective amount").

As used herein, an "effective amount" means the dose or amount of a pharmaceutical or nutraceutical composition that includes a stable sulforaphene administered to a subject that results in the reduction or eradication of a mitochondrial or muscular disorder or symptom thereof. The effective amount of a composition can be readily determined by one of ordinary skill in the art, by the use of known techniques and by observing results obtained under analogous circumstances.

In one exemplary embodiment, an effective amount of a pharmaceutical or nutraceutical composition that includes a stable sulforaphene administered to a subject is any amount that results in the increase of ATP production by the cells of the subject.

In another embodiment, an effective amount of a pharmaceutical or nutraceutical composition that includes a stable sulforaphene administered to a subject is any amount greater than 2 µg/mL resulting in an increase of FAD by the subject's muscle cells.

The effective amount of a pharmaceutical or nutraceutical composition comprised of stabilized sulforaphene (e.g., sulforaphene/cyclodextrin complex), can depend on a number of factors, such as the specific stabilizing agent or method used, the subject, the mode of administration, and the disorder being treated. For example, the dosage may be adjusted based on the subject's weight, the age and health of the subject, and tolerance for the composition being administered.

Certain, non-limiting examples of suitable dosage ranges for injection of pharmaceutical composition include, but are not limited to, a dose of 0.06 mg/kg/day for an individual having a body weight of 40 kg or less, and such dose may increase or decrease by 0.02 mg/kg to a maximum daily dose of 0.13 mg/kg, a dose of 2.5 mg/day individual having a body weight greater than 40 kg, and such dose may increase or decrease by 1.25 mg to 2.5 mg/day to a maximum dose of 10 mg/day, for females having a body weight greater than 40 kg, a dose of 5 mg/day is appropriate, and such dose may increase or decrease by 1.25 mg to 2.5 mg/day to a maximum dose of 10 mg/day. In yet another example, the pharmaceutical composition of the present disclosure can be delivered to a subject in 30 mcg/mL, 60 mcg/mL, 90 mcg/mL, or 120 mcg/mL doses.

In other examples, dosages for the present compositions and methods provided herein may be determined and adjusted based on the efficacy demonstrated in providing a therapeutic effect. In addition, one of ordinary skill in the art will know how to measure and quantify the presence or absence of a mitochondrial or muscular disorder or symptoms thereof after treatment according to the present methods. In some instances, a therapeutically effective amount will ameliorate or reduce one or more of the following aberrant conditions in a subject having a mitochondrial disorder: mitochondrial oxidative metabolism, amino acid metabolism, organic acid metabolism, ATP production by cells (e.g., skin cells or muscle cells), cellular viability, fatty acid metabolism, carbohydrate metabolism, urea formation and peroxisomal metabolism.

For example, in the case of a mitochondrial myopathy, such as chronic fatigue syndrome or essential tumor, an effective amount of stable sulforaphene will reduce or abolish an irregularity in cellular metabolism, increase mitochondrial function (i.e., ATP production), increase excretion of one or more amino acids, or any combination of the foregoing conditions.

In the case of a skin disorder such as psoriasis, aging skin or psoriatic arthritis, an effective treatment can ameliorate a skin lesion or inflammation.

In the case of PCOS, an effective treatment with a stable sulforaphene/cyclodextrin complex will reduce or abolish one or more of the following in the subject, irregular periods, abnormal androgen, polycystic ovaries or a related condition as set forth below.

In some instances, a therapeutically effective amount will ameliorate or reduce one or more of the following aberrant conditions in a subject having a muscular disorder: reduced levels of FAD produced by the subjects muscle cells or a reduced amount of ATP produced by such cells.

For example, in the case of a myopathy, such as chronic fatigue syndrome or essential tumor, an effective amount of stable sulforaphene will increase ATP production in muscle tissue, and/or increase the level of FAD present in muscle cells or a combination thereof.

In certain instances, the amount of stabilized sulforaphene effective to treat a muscular disorder by increasing the level of FAD in a subject's muscle cells is greater than 2 µg/mL, between 2.1 µg/mL, and 17.5 µg/mL or 17.5 µg/mL. In other instances, an effective amount of a pharmaceutical or nutraceutical composition comprises 2.1 µg/mL, 2.5 µg/mL, 3.0 µg/mL, 3.5 µg/mL, 4.0 µg/mL, 4.5 µg/mL, 5.0 µg/mL, 5.5 µg/mL, 6.0 µg/mL, 6.5 µg/mL, 7.0 µg/mL, 7.5 µg/mL, 8.0 µg/mL, 8.5 µg/mL, 9.0 µg/mL, 9.5 µg/mL, 10.0 µg/mL, 10.5 µg/mL, 11.0 µg/mL, 11.5 µg/mL, 12.0 µg/mL, 12.5 µg/mL, 13.0 µg/mL, 13.5 µg/mL, 14.0 µg/mL, 14.5 µg/mL, 15.0 µg/mL, 15.5 µg/mL, 16.0 µg/mL, 16.5 µg/mL, 17.0 µg/mL, 17.5 µg/mL, or greater of a sulforaphene and hydroxypropyl-beta-cyclodextrin complex.

Effective doses may also be extrapolated from dose-response curves derived from in vitro or animal model systems, such as in a mouse model. Those skilled in the art will appreciate that dosages may also be determined with guidance from Goodman & Gilman's *The Pharmacological Basis of Therapeutics*, Ninth Edition (1996), Appendix II, pp. 1707-1711.

The pharmaceutical or nutraceutical compositions of the present disclosure can be administered as needed, once or multiple times per day. The frequency of administration may vary from a single dose per day to multiple doses per day. In one embodiment, the composition can be administered once a week, once every two weeks, once every three weeks, once a month, bimonthly or biannually. In certain embodiments, the composition can be administered, for example, when a subject with mitochondrial or muscle disorder presents inflammation, a skin lesion, muscle tremors, fatigue, a reduced amount of FAD when compared to other muscle cells or other symptoms that would warrant administration of treatment.

In one aspect, the present methods include the treatment of a mitochondrial disorder. In another aspect, the present methods include the treatment of a muscular disorder.

The term "treatment," refers to a prevention or amelioration of a disorder, or one or more symptoms thereof, in a patient or a subject. It is not intended that "treating" a disorder requires curing or eradicating it completely. It is only necessary that the treatment reduce or inhibit the disorder, i.e., having a "therapeutic effect". Similarly, the progression of a disorder is considered herein to be "reduced" or "inhibited" if, in the judgment of a practitioner, one or more of the characteristic indicia of progression of the disorder are reduced or inhibited. The term "therapeutic effect" refers to the inhibition, activation or replacement of factors causing or contributing to a disorder or symptom thereof in a subject.

The term "mitochondrial disorder" or "mitochondrial disease" are used interchangeably herein to refer to the disorders or defects that occur when the cells of a subject are unable to properly metabolize carbohydrates, lipids (fats), proteins, or nucleic acids by oxidative phosphorylation. Accordingly, in the context of the present methods all the disorders relating to abnormality of a subject's ability to generate ATP are encompassed in the term "mitochondrial disorders". Examples of mitochondrial disorders include, but are not limited to, mitochondrial myopathy, metabolic disorders, skin disorders, prostate disorders, or disorders of the central nervous system. For the purposes of this disclosure, it is not intended that a metabolic disorder include cancer.

Exemplary mitochondrial disorders that can be treated by the present methods include, but are not limited to, mitochondrial myopathy. As used herein the term "mitochondrial myopathy" shall mean a dysfunction in the production of ATP by oxidative phosphorylation of mitochondria by muscle cells and/or cells of the central nervous system (CNS) of a subject. The symptoms of mitochondrial myopathies include muscle weakness or exercise intolerance, heart failure or rhythm disturbances, dementia, movement disorders, stroke-like episodes, deafness, blindness, droopy eyelids, limited mobility of the eyes, vomiting, and seizures. Several exemplary mitochondrial myopathies, which can be treated by the administration of an effective amount of a sulforaphene/hydroxypropyl-beta-cyclodextrin complex include, but are not limited to chronic fatigue syndrome (CFS), prostatic disease (i.e., prostate hyperplasia), essential tremor, Parkinson's disease, and multiple sclerosis.

In an exemplary embodiment, the subject being administered a composition composed of a stabilized sulforaphene, such as sulforaphene/hydroxypropyl-beta-cyclodextrin complex, according to the present disclosure has a mitochondrial myopathy such as chronic fatigue syndrome (CFS). "Chronic fatigue syndrome (CFS)" as used herein means a mitochondrial disorder that presents as long-term physical and mental fatigue. CFS is associated with one or more of the following symptoms: pain and increased sensitivity, aberrant metabolism (e.g., energy metabolism, amino acid metabolism, nucleotide metabolism, nitrogen metabolism, hormone metabolism, and oxidative stress metabolism), reduced mitochondrial function, reduced excretion of amino acids and nitrogen by cells. A subject can be readily diagnosed with CFS by one of ordinary skill in the art using known methods to detect changes in cellular metabolism by the mitochondria such as ATP production or cell viability by use of metabolomics.

In an exemplary embodiment, the subject being administered a composition composed of a stabilized sulforaphene, such as sulforaphene/hydroxypropyl-beta-cyclodextrin complex, according to the present disclosure has a mitochondrial myopathy such as prostate disease. "Prostate hyperplasia" or "prostate disease" are used interchangeably herein to mean a mitochondrial disorder that presents as an enlarged prostate gland, such as is present in "benign prostate hyperplasia (BPH)". Prostate hyperplasia is associated with one or more of the following symptoms: reduced or blocked flow of urine from the bladder, an increased frequency of urination, an inability to empty the bladder, a urinary tract infection, or blood in the urine. A subject can be readily diagnosed with BPH by one of ordinary skill in the art using known methods to detect changes in cellular metabolism by the mitochondria such as ATP production or cell viability by use of metabolomics.

Mitochondria play an essential role in providing the energy necessary for dopaminergic neurons to function properly. Therefore, in some embodiments of the present disclosure a subject being administered a composition composed of a stabilized sulforaphene, such as sulforaphene/hydroxypropyl-beta-cyclodextrin complex, as a mitochondrial myopathy of the central nervous system. Exemplary mitochondrial myopathies of the central nervous system include, but are not limited to, essential tremor, multiple sclerosis, dementia and Parkinson's disease.

In an exemplary embodiment, the subject being administered a composition composed of a stabilized sulforaphene, such as sulforaphene/hydroxypropyl-beta-cyclodextrin complex; according to the present disclosure has a mitochondrial myopathy such as essential tremor. The term "essential tremor" as used herein shall mean a neurological disorder that causes involuntary and rhythmic shaking of the extremities. Essential tremor is evident when hands, head or voice shake involuntarily during use or a subject exhibits an aberrant gait.

In one embodiment, the subject being administered a composition composed of a stabilized sulforaphene, such as sulforaphene/hydroxypropyl-beta-cyclodextrin complex, according to the present disclosure has a mitochondrial myopathy such as multiple sclerosis (MS). The term "multiple sclerosis" as used herein means a neurodegenerative disorder, caused by abnormalities in mitochondrial oxidative phosphorylation that results in a reduction in ATP production, leading to axonal injury, neuronal loss (reduced cell viability and atrophy of the central nervous system.

Mitochondrial function also regulates hormone production by the endocrine system. The thyroid gland is located at the front of neck and secretes 2 types of thyroid hormones: T4 (Thyroxine) and T3 (Triiodothyronine). Thyroid hormones are known to regulate the basal metabolic state and oxidative metabolism of cells. For example, thyroid hormones are associated with oxidative stress and antioxidant status due to their ability to change oxidative respiration in mitochondria. Moreover, the thyroid can product hormones that signal oxidative stress, which results in a decrease in ATP production by the mitochondria, and thus cell death. Such oxidative stresses are present in, for example, polycystic ovary syndrome (PCOS), mitochondrial diabetes, hypothyroidism and hyperthyroidism.

Therefore, in an exemplary embodiment, the subject being administered a composition composed of a stabilized sulforaphene, such as sulforaphene/hydroxypropyl-beta-cyclodextrin complex, according to the present disclosure has PCOS. "Polycystic ovary syndrome" as used herein means a mitochondrial disorder that presents in women subjects having one or more of the following symptoms, irregular periods, abnormal androgen and polycystic ovaries. PCOS also presents with other common disorders ("related symptoms or conditions") such as insulin resistance, obesity, glucose intolerance, dyslipidemia, and/or hypertension.

Mitochondria play an essential role in providing the energy necessary for skin cells to function properly. Therefore, in some embodiments of the present disclosure a subject being administered a composition composed of a stabilized sulforaphene, such as sulforaphene/hydroxypropyl-beta-cyclodextrin complex, as a mitochondrial myopathy of the skin. Exemplary mitochondrial myopathies of the skin include, but are not limited to, psoriasis, psoriatic arthritis, skin aging.

Therefore, in one embodiment, the subject being administered a composition composed of a stabilized sulforaphene, such as sulforaphene/hydroxypropyl-beta-cyclodextrin complex, according to the present disclosure has a mitochondrial myopathy such as psoriasis. The term "psoriasis" as used herein refers to a Th-1 and Th-17-mediated disease that has been associated with mitochondrial disorders. Psoriasis is characterized by presentation of inflamed, irritated, scaling of the skin and one or more of the following, dry lesions, stiff or swollen joints, obesity, hypertension, dyslipidemia, and insulin resistance diseases.

In another embodiment, the subject being administered a composition composed of a stabilized sulforaphene, such as sulforaphene/hydroxypropyl-beta-cyclodextrin complex, according to the present disclosure has a mitochondrial myopathy such as aging skin. The term "aging skin" as used herein shall mean a progressive structural and functional degeneration of the skin epidermis. Aging skin is caused primarily by the buildup of reactive oxygen species (ROS) as a by-product of cellular metabolism of the mitochondria ROS, in turn, cause damage to critical cellular components like membranes, enzymes, and deoxyribonucleic acid (DNA) resulting in cell death. Furthermore, in the aging skin cellular proliferation rates decrease in the epidermis, inducing a steady deterioration of skin structure and function. Aging skin can be a precursor to other skin disorder, such as eczema, dermatitis, keratoses, and various forms of neoplasms, such as basal and squamous cell carcinoma and malignant melanoma.

In other embodiments, the subject being administered a composition composed of a stabilized sulforaphene, such as sulforaphene/hydroxypropyl-beta-cyclodextrin complex, according to the present disclosure has a muscular disorder.

The term "muscle disorder" or "muscular disorder" or "muscle disease" are used interchangeably herein to refer to the disorders or defects that occur when the muscle cells of a subject exhibit aberrant function and/or tone. In some instances, a subject's muscle cells fail to properly contract or generate enough energy to function properly. Accordingly, in the context of the present methods all the muscular disorders relating to abnormality of a subject's ability to generate ATP and/or FAD are encompassed in the term "muscular disorder". Examples of muscular disorders include, but are not limited to, myotonia and myopathies. In specific instances, the muscular disorder is an infection of muscle tissue such as, for example, by a virus or bacteria.

Exemplary muscular disorders that can be treated by the present methods include, but are not limited to, muscular dystrophy, or motor neuron diseases such as Amyotrophic lateral sclerosis (ALS) and poly myositisis. In other instances, the muscular disorder being treated is chronic fatigue syndrome, metabolic diseases of the muscle such as, for example, Phosphorylase deficiency (McArdle disease), Acid maltase deficiency (Pompe disease), Phosphofructokinase deficiency (Tarui disease), Debrancher enzyme deficiency (Cori or Forbes disease), Mitochondrial myopathy, Carnitine deficiency, Carnitine palmityl transferase deficiency, Phosphoglycerate kinase deficiency, Phosphoglycerate mutase deficiency, Lactate dehydrogenase deficiency, and Myoadenylate deaminase deficiency.

In one embodiment the subject being treated has a myopathy. The symptoms of which can include muscle weakness or exercise intolerance, heart failure or rhythm disturbances, dementia, movement disorders, stroke-like episodes, deafness, blindness, droopy eyelids, limited mobility of the eyes, vomiting, and seizures. Several exemplary myopathies, which can be treated by the administration of an effective amount of a sulforaphene/hydroxypropyl-beta-cyclodextrin complex include, but are not limited to chronic fatigue syndrome (CFS), prostatic disease (i.e., prostate hyperplasia), essential tremor, Parkinson's disease, and multiple sclerosis.

In an exemplary embodiment, the subject being administered a composition composed of a stabilized sulforaphene, such as sulforaphene/hydroxypropyl-beta-cyclodextrin complex, according to the present disclosure has a myopathy such as chronic fatigue syndrome (CFS). A subject can be readily diagnosed with CFS by one of ordinary skill in the art using known methods to detect changes in FAD production or cell viability by use of metabolomics.

In another embodiment, the muscular disorder being treated by the administration of a composition composed of a stabilized sulforaphene, such as sulforaphene/hydroxypropyl-beta-cyclodextrin complex, is muscular dystrophy. In specific embodiments, the muscular dystrophy is Myotonic dystrophy (Steinert disease), Duchenne muscular dystrophy, Becker muscular dystrophy, Limb-girdle muscular dystrophy, Facioscapulohumeral muscular dystrophy, Congenital muscular dystrophy, Oculopharyngeal muscular dystrophy, Distal muscular dystrophy, or Emery-Dreifuss muscular dystrophy.

In other embodiments, the muscular disorder being treated by the administration of a composition composed of a stabilized sulforaphene, such as sulforaphene/hydroxypropyl-beta-cyclodextrin complex, is a motor neuron disease such as Amyotrophic lateral sclerosis (ALS) and poly myositisis.

Methods for Increasing FAD.

In one aspect of the present disclosure, methods for increasing the amount of FAD in a muscle cell are provided. Here, it has been determined that the administration of compositions composed of stable sulforaphene prolongs the bioactivity of sulforaphene and significantly improves a muscle cell's ability to produce FAD. For example, surprisingly, it has been shown that administration of greater than 2 µg/mL of a stable sulforaphene results in a significant increase in the amount of FAD produced by muscles cells when compared to both negative controls and cells that have been administered 2 µg/mL or less of stabilized sulforaphene. See FIG. 4. As such, the present disclosure provides a method for increasing the levels of FAD in a cell that includes administering to the cell a stabilized sulphoraphene, and detecting the level of FAD in the cell.

In certain embodiments, the present disclosure provides a method for increasing FAD in a muscle cell by the administration of greater than 2 µg/mL of a stabilized sulforaphene.

The foregoing stabilized sulforaphene compositions can be formed and administered as provided herein.

In some embodiments, the stabilized sulforaphene is administered to muscle cells in an amount greater than 2 µg/mL. In another embodiment, the stabilized sulforaphene consists of greater than 2 µg/mL of a sulforaphene and hydroxypropyl-beta-cyclodextrin complex. In one embodiment, the stabilized sulforaphene consists essentially of between 2.1 µg/mL and 17.5 µg/mL of a sulforaphene and hydroxypropyl-beta-cyclodextrin complex. In other embodiments, the stabilized sulforaphene comprises 17.5 µg/mL of a sulforaphene and hydroxypropyl-beta-cyclodextrin complex. In one embodiment, the stabilized sulforaphene consists essentially of 17.5 µg/mL of a sulforaphene and hydroxypropyl-beta-cyclodextrin complex.

In specific embodiments, the stabilized sulforaphene comprises 2.1 µg/mL, 2.5 µg/mL, 3.0 µg/mL, 3.5 µg/mL, 4.0 µg/mL, 4.5 µg/mL, 5.0 µg/mL, 5.5 µg/mL, 6.0 µg/mL, 6.5 µg/mL, 7.0 µg/mL, 7.5 µg/mL, 8.0 µg/mL, 8.5 µg/mL, 9.0 µg/mL, 9.5 µg/mL, 10.0 µg/mL, 10.5 µg/mL, 11.0 µg/mL, 11.5 µg/mL, 12.0 µg/mL, 12.5 µg/mL, 13.0 µg/mL, 13.5 µg/mL, 14.0 µg/mL, 14.5 µg/mL, 15.0 µg/mL, 15.5 µg/mL, 16.0 µg/mL, 16.5 µg/mL, 17.0 µg/mL, 17.5 µg/mL, or greater of a sulforaphene and hydroxypropyl-beta-cyclodextrin complex.

Once a stabilized sulforaphene is administered to a muscle cell, the level of FAD in the cell is detected. In some instances, the amount of FAD produced by a muscle cell is detected by fluorometric or colormetric methods, however other methods of detecting FAD in cells are applicable and known by those of ordinary skill in the art.

In one instance, FAD can be detected using a colormetric assay. For example, cells can be treated with an amount of stabilized sulforaphene for a predetermined period of time. The cells are then lysed and deproteinized with perchloric acid. The cell lysis mixture can then be processed and the concentration of FAD in the cellular extracts can be measured by a colorimetric assay based on detection of an FAD-dependent reaction using a spectrophotometer. In some instances, the probe emits a signal after it oxidizes in the presence of FAD.

The foregoing detection methods can be carried out in a test sample of cells. In some instances, the amount of FAD produced by cells can be detected in a test sample of muscle cells and a control sample of muscle cells (i.e., cells that have not been treated with a stabilized sulforaphene or treated with 2 μg/mL, or less of a stabilized sulforaphene).

In certain instances, the present methods include treating muscle cells with greater than 2 μg/mL of a stabilized sulforaphene, determining the amount of FAD produced by the treated cells and comparing the amount of FAD to control levels of FAD.

In some instances the cells being administered greater than 2 μg/mL of a stabilized sulforaphene are muscle cells. Non-limiting examples of muscle cells for use in the present methods include mammalian muscle cells, such as murine, rat or human muscle cells. In certain embodiments, the muscle cells are myoblasts, smooth muscle cells (e.g., cardiac cells) or skeletal muscle. In a specific embodiment, the cells are A-204 human muscle cells.

Other embodiments within the scope of the claims herein will be apparent to one skilled in the art from consideration of the specification or practice of the methods as disclosed herein. It is intended that the specification and experimental results that follow be considered exemplary only, with the scope and spirit of the invention being indicated by the claims to follow.

EXAMPLES

Example 1. Materials and Methods

Cell cultures. For all cell based assays the following cell lines and culture methods were used. SK-MEL-31 human skin cells and A204 human muscle cells were obtained from ATCC®, cultured and maintained in MoCoy-5A medium with 10% FBS, as well as 1% Penicillin and Streptomycin. PANC-1 human pancreatic cancer cells were obtained from ATCC®, cultured and maintained in DMEM Medium with 10% FBS as well as 1% Penicillin and Streptomycin.

Prior to plating on 96-well plates, cells were trypsinized and counted using a cell counter (Countess® Automated Cell Counter, Invitrogen). Cells were then suspended to the appropriate cell density for each cell type tested prior to seeding. Specifically, the cell suspensions were formulated to include 15,000 cells per 100 uL of cell media for both SK-MEL-31 and A204 cells, and 12,000 cells per 100 uL of cell media for PANC-1 cells. 100 uL of cell suspension was then seeded in each well of white wall, tissue culture treated 96-well plates (Corning) and maintained for 24 hours at 37° C.

Cell Titer-Glo (CTG) ATP Assay. After 24 hour cell seeding, cells were administered a ⅓ dilution of 100 uL of 1 uM staurosporine (Sigma-Aldrich) and one of the following compositions using a Tecan D300e Digital Dispenser (Tecan); 100 uM synthetic sulforaphene/hydroxypropyl-beta-cyclodextrin complex (Compound 1); 17.5 ug/ml sulforaphene isolated from radish seed extract (Compound 2) and 17.5 ug/ml positive control (Compound 3). A total of 9 places were used for each cell line tested.

After cells were treated with a test compound for either 4 hours (data not shown), 48 hours or 72 hours, cells were left at room temperature for approximately 30 minutes. Then, 100 μl of CellTiter-Glo Reagent (Promega) was added to each well of a plate and each plate was mixed for 2 minutes on an orbital shaker to induce cell lysis. After shaking each plate was incubated at room temperature for 10 minutes to stabilize a luminescent signal. Then the signal was read according to manufacturers protocol on an EnVision Multilabel Reader (Perkin Elmer). The effect of each composition on mitochondrial function was determined based on a quantification of the ATP present in each well, whereby the amount of ATP present s directly proportional to the amount of cells present in each well. Specifically, the effect of each compound was calculated using the following formula: Effect %=(X-control media only)/(control-control DMSO effect)×100%.

FAD Detection Assay. After 24 hour cell seeding, cells were administered one of the following compositions using a Tecan D300e Digital Dispenser (Tecan): 10 nM staurosporine (Sigma-Aldrich) as a positive control, synthetic sulforaphene/hydroxypropyl-beta-cyclodextrin complex (Compound 1) or water as a negative control.

After cells were treated, they were incubated for 96 hours and FAD was detected using the using FAD Assay Kit (ab204710; Abcam) according to manufacturer protocol. Briefly, cells were collected, lysed and deproteinized with perchloric acid, and the resulting samples were mixed with the reaction mixture. The concentration of FAD was measured by a colorimetric assay based on the FAD-dependent reaction of OxiRed probe using a spectrophotometer (iMark microplate reader; Bio-Rad). The effect of each composition on FAD production was determined.

Example 2. Stable Sulforaphene Results Increases Mitochondrial ATP Production in Skin Cells In order to determine whether stabilized sulforaphene, i.e., synthetic sulforaphene/hydroxypropyl-beta-cyclodextrin complex was capable of treating mitochondrial disorders of the skin, such as psoriasis, or skin aging, a CellTiter-Glo® Luminescent Cell Viability Assay was carried out on SK-MEL-31 human skin cells, as described above. This assay determined the number of viable skin cells present in each well by measuring the amount of ATP present in each well. Briefly, detection was based on using a luciferase reaction to measure the amount of ATP present from viable cells. If mitochondrial function, i.e., ATP production from oxidative phosphorylation, increased after administration of stable sulforaphene when compared to cells treated with staurosporine alone, then the exemplary stabilized sulforaphene composition can be used to treat mitochondrial disorders of the skin.

Staurosporine (STSP) is a cell permeable alkaloid isolated from *Streptomyces staurosporeus*. Staurosporine is a potent, non-selective inhibitor of protein kinases, including protein kinase C, which induces apoptosis in cells. Therefore, cells treated with Staurosporine alone were used as a negative control.

Figure 1B:
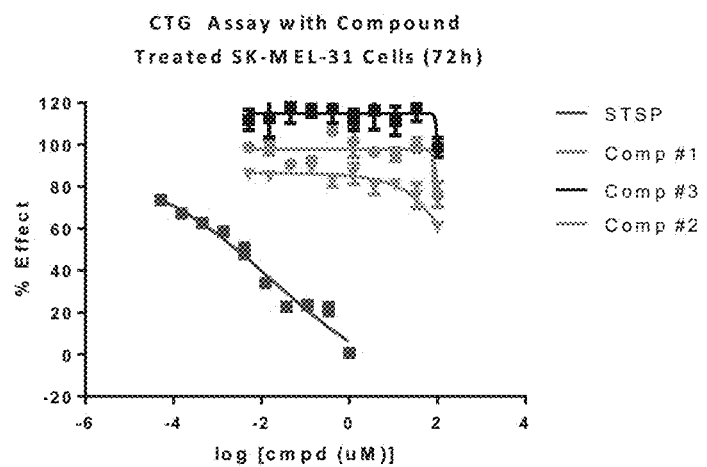

After treatment with STSP, SK-MEL-31 human skin cells were administered 100 uM of synthetic sulforaphene/hydroxypropyl-beta-cyclodextrin complex (compound 1), 17.5 ug/mL of sulforaphene isolated from radish seed extract (compound 2), or 17.5 ug/mL of positive control (compound 3) and incubated for either 4 hours (data not shown), 48 hours or 72 hours as shown in FIGS. 1A-1B.

The data shown in FIGS. 1A-1B show that both compounds including stabilized sulforaphene (i.e., compound 1 and compound 2) result in an increase of ATP production in skin cells after treatment with STSP that is comparable to that exhibited after treatment with positive control compound (compound 3). Therefore, it has been shown that stabilized sulforaphene compositions of the present disclosure increase mitochondrial function by increasing oxidative phosphorylation and ATP production in vitro. Taken together, these data show that stabilized sulforaphene compositions of the present disclosure can be used to treat mitochondrial disorders of the skin, such as psoriasis and skin aging.

Example 3. Stable Sulforaphene Results Increases Mitochondrial ATP Production in Muscle Cells In order to determine whether stabilized sulforaphene, i.e., synthetic sulforaphene/hydroxypropyl-beta-cyclodextrin n complex was capable of treating mitochondrial myopathy in muscle tissue, such as chronic fatigue syndrome (CFS), essential tremor, or Parkinson's a CellTiter-Glo® Luminescent Cell Viability Assay was carried out on A204 human muscle cells, as described above. Experiments were carried out as set forth in Example 2, above. Therefore, if mitochondrial function, i.e., ATP production from oxidative phosphorylation, increased after administration of stable sulforaphene when compared to cells treated with staurosporine alone, then the exemplary stabilized sulforaphene composition could be used to treat muscular mitochondrial myopathy.

Figure 2A:
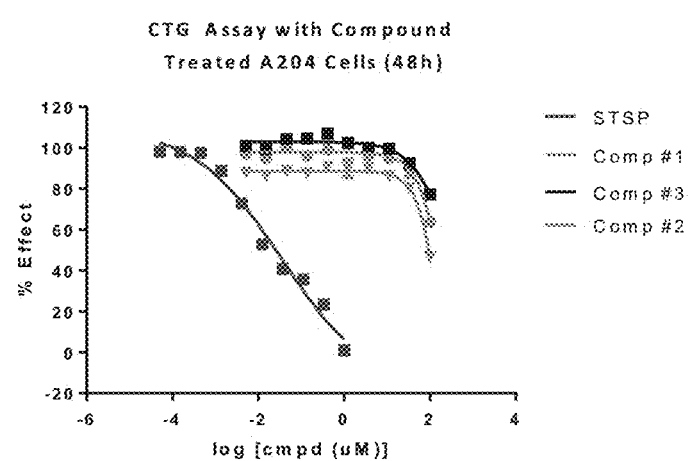
FIGS. 2A-2B. Stabilized sulforaphene induces mitochondrial ATP production in muscle. A204 human muscle cells were cultured and plated in 96-well plates at a cell density of 15,000 cells per well. Cells were then treated with staurosporine (STSP), a known inhibitor of mitochondrial function and ATP production. After incubation with STSP, cells were then administered either 100 µM of a sulforaphene and hydroxypropyl-beta-cyclodextrin complex (compound 1), 17.5 µg/µL of a stabilized sulforaphene composition isolated from radish seed extract (compound 2) or 17.5 µg/µL of a positive control known to induce ATP production (compound 3). Cells were then incubated for 4 hours (data not shown), 48 hours (A) or 72 hours (B). Muscle cells treated with stabilized sulforaphene compositions exhibited an increase in mitochondrial function similar to that of cells treated with a positive control and significantly above that of cells treated with STSP alone.
Figure 2B:
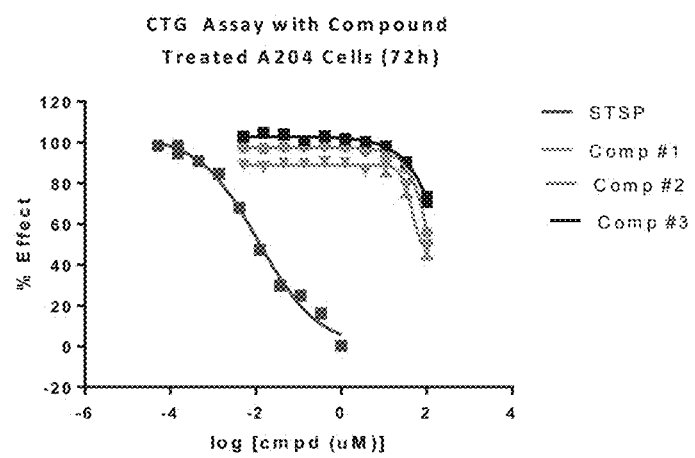

After treatment with STSP, A204 human muscle cells were administered 100 uM of synthetic sulforaphene/hydroxypropyl-beta-cyclodextrin complex (compound 17.5 ug/mL of sulforaphene isolated from radish seed extract (compound 2), or 17.5 ug/mL of positive control (compound 3) and incubated for either 4 hours (data not shown), 48 hours or 72 hours as shown in FIGS. 2A-2B.

The data shown in FIGS. 2A-2B show that both compounds including stabilized sulforaphene (i.e., compound 1 and compound 2) result in an increase of ATP production in muscle cells after treatment with STSP that is comparable to that exhibited after treatment with positive control compound (compound 3). Therefore, it has been shown that stabilized sulforaphene compositions of the present disclosure increase mitochondrial function by increasing oxidative phosphorylation and ATP production in vitro. Taken together, these data show that stabilized sulforaphene compositions of the present disclosure can be used to treat mitochondrial myopathies, such as CFS and essential tremor.

Example 4. Stable Sulforaphene Results Increases Mitochondrial ATP Production in Other (Pancreatic) Cells In order to determine whether stabilized sulforaphene, i.e., synthetic suforaphene/hydroxypropyl-beta-cyclodextrin complex was capable of treating mitochondrial disorders in other cell types, such as the pancreas which modulate endocrine function, a CellTiter-Glo® Luminescent Cell Viability Assay was carried out on PANC-1 human pancreatic cells, as described above. Experiments were carried out as set forth in Examples 2 and 3, above. Therefore, if mitochondrial function, i.e., ATP production from oxidative phosphorylation, increased after administration of stable sulforaphene when compared to cells treated with staurosporine alone, then the exemplary stabilized sulforaphene composition could be used to treat mitochondrial disorders from other organs, or that are hormone based, such as PCOS, prostate myopathies, and thyroid disorders.

Here, as in Examples 2 and 3, after treatment with STSP, PANC-1 cells were administered 100 uM of synthetic sulforaphene/hydroxypropyl-beta-cyclodextrin complex (compound 1), 17.5 ug/mL of sulforaphene isolated from radish seed extract (compound 2), or 17.5 ug/mL of positive control (compound 3) and incubated for either 4 hours (data not shown), 48 hours or 72 hours.

Figure 3A:
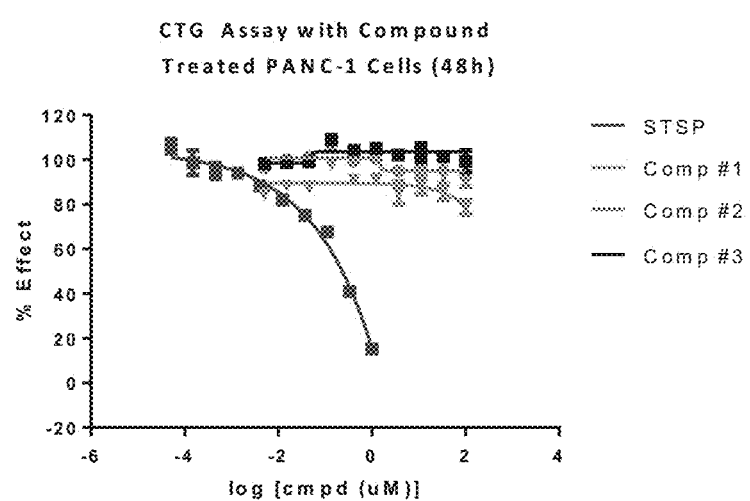
FIGS. 3A-3B. Stabilized sulforaphene induces mitochondrial ATP production in pancreatic cells. PANC-1 human pancreatic cells were cultured and plated in 96-well plates at a cell density of 15,000 cells per well. Cells were then treated with staurosporine (STSP), a known inhibitor of mitochondrial function and ATP production. After incubation with STSP, cells were then administered either 100 µM of a sulforaphene and hydroxypropyl-beta-cyclodextrin complex (compound 1), 17.5 µg/µL of a stabilized sulforaphene composition isolated from radish seed extract (compound 2) or 17.5 µg/µL of a positive control known to induce ATP production (compound 3). Cells were then incubated for 4 hours (data not shown), 48 hours (A) or 72 hours (B). Pancreatic cells treated with stabilized sulforaphene compositions exhibited an increase in mitochondrial function similar to that of cells treated with a positive control and significantly above that of cells treated with STSP alone.
Figure 3B:
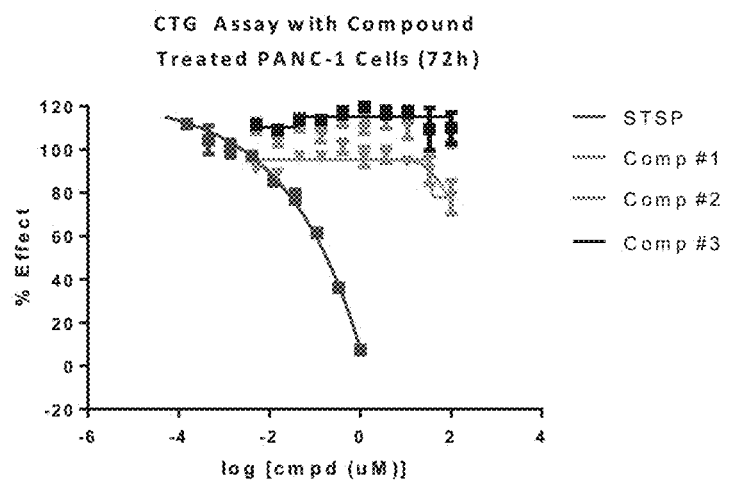

The data shown in FIGS. 3A-3B show that both compounds including stabilized sulforaphene (i.e., compound 1 and compound 2) result in an increase of ATP production in pancreatic cells after treatment with STSP that is comparable to that exhibited after treatment with positive control compound (compound 3). Therefore, it has been shown that stabilized sulforaphene compositions of the present disclosure increase mitochondrial function by increasing oxidative phosphorylation and ATP production in vitro. Taken together, these data show that stabilized sulforaphene compositions of the present disclosure can be used to treat mitochondrial disorders in other tissue such as the pancreas.

Example 5. Stable Sulforaphene Results Increases FAD Levels in Muscle Cells

In order to determine whether stabilized sulforaphene, i.e., synthetic sulforaphene/hydroxypropyl-beta-cyclodextrin complex was capable of treating muscular disorders, A204 human muscle cells were treated with 100 nM staurosporine (STSP) as a positive control, 17.5 ug/mL, of stable sulforaphene, 2.0 µg/mL of stable sulforaphene or water (as a negative control), as described above. The levels of FAD produced by all cells tested were then detected as set forth in Example 1.

Figure 4:
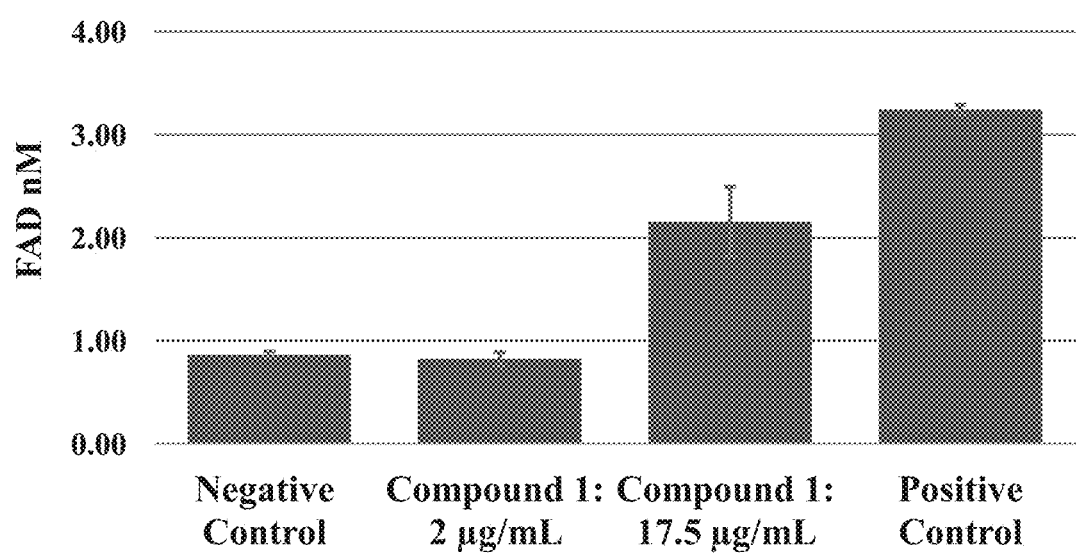
FIG. 4. Stabilized sulforaphene increases FAD levels in production in muscle. A204 human muscle cells were cultured and plated in 6-well plates at a cell density of 15,000 cells per well. Cells were then treated with one of: 10 nM of a positive control (i.e., staurosporine), 2 µg/mL of a sulforaphene and hydroxypropyl-beta-cyclodextrin complex (compound 1: 2 µg/mL), 17.5 µg/mL of a sulforaphene and hydroxypropyl-beta-cyclodextrin complex (compound 1: 17.5 µg/mL or a negative control for 4 days, and then FAD levels were measured in each cell culture. Muscle cells treated with greater than 2 µg/mL stabilized sulforaphene compositions exhibited an increase FAD production when compared to control cells.

The data shown in FIG. 4 shows, surprisingly, that administration of 17.5 ug/mL of stable sulforaphene but not 2.0 ug/mL of stable sulforaphene resulted in an increase in FAD production by muscle cells comparable to those observed in cells treated with positive control. Interestingly, administration of 2.0 ug/mL stable sulforaphene to muscle cells did not result in a significant increase in FAD production when compared to cells treated with a negative control. Therefore, it has been shown that stabilized sulforaphene compositions of the present disclosure increase muscle cell function by increasing FAD production in muscle cells in vitro. Taken together, these data show that stabilized sulforaphene compositions of the present disclosure can be used to treat muscular disorders mediated by aberrations in FAD production.

What is claimed is:

1. A method for increasing flavin adenine dinucleotide (FAD) in a cell comprising:
   administering a stable sulforaphene composition to a cell, wherein said stable sulforaphene composition comprises isolated sulforaphene and a stabilizing agent; and
   detecting the amount of FAD present in the cell, wherein said administration increases FAD production by the cell when compared to a cell that is not administered a stable sulforaphene composition.

2. The method of claim 1, wherein the cell is a muscle cell.

3. The method of claim 2, wherein the stable sulforaphene composition comprises a sulforaphene/cyclodextrin complex.

4. The method of claim 3, herein the sulforaphene/cyclodextrin complex consists of a sulforaphene and a hydroxypropyl-beta-cyclodextrin.

5. The method of claim 3, wherein the cyclodextrin is beta cyclodextrin or a hydroxyalkyl derivate thereof.

6. The method of claim 3, wherein the sulforaphene/cyclodextrin complex is administered in an amount greater than 2 µg/mL.

7. The method of claim 6, wherein the sulforaphene/cyclodextrin complex is administered in an amount between 2.1 μg/mL and 17.5 μg/mL.

8. The method of claim 7, wherein 17.5 μg/mL sulforaphene/cyclodextrin complex is administered to the cell.

9. The method of claim 1, wherein said detection comprises:
   obtaining a sample of the cells that have been treated with the stable sulforaphene;
   administering an oxidase to said sample, wherein said oxidase reacts with FAD to generate a detectable signal; and
   measuring the detectable signal generated by the sample.

10. The method of claim 9, wherein the oxidase comprises a fluorometric probe or a colormetric probe, and wherein the fluorometric probe or colormetric probe emits said detectable signal.

* * * * *